(12) United States Patent
Chauvin et al.

(10) Patent No.: US 7,915,426 B2
(45) Date of Patent: Mar. 29, 2011

(54) IMIDAZOLIUM SALTS AND THEIR USE OF THESE IONIC LIQUIDS AS A SOLVENT

(75) Inventors: Yves Chauvin, Tours (FR); Lionel Magna, Hyeres (FR); Gerald Peter Niccolai, Villeurbanne (FR); Jean-Marie Basset, Caluire (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 1850 days.

(21) Appl. No.: 10/399,908

(22) PCT Filed: Oct. 25, 2001

(86) PCT No.: PCT/IB01/02003
§ 371 (c)(1),
(2), (4) Date: Apr. 24, 2003

(87) PCT Pub. No.: WO02/34722
PCT Pub. Date: May 2, 2002

(65) Prior Publication Data
US 2004/0026666 A1 Feb. 12, 2004

(30) Foreign Application Priority Data
Oct. 27, 2000 (EP) .................................... 00403008

(51) Int. Cl.
*C07D 233/64* (2006.01)
*C07D 233/66* (2006.01)
(52) U.S. Cl. .................. 548/342.5; 548/343.1
(58) Field of Classification Search ............... 548/342.5, 548/343.1
See application file for complete search history.

(56) References Cited

U.S. PATENT DOCUMENTS

| 5,041,194 A | 8/1991 | Mori et al. | |
| 5,683,832 A | 11/1997 | Bonhote et al. | |
| 5,827,602 A * | 10/1998 | Koch et al. | 429/328 |
| 6,025,457 A * | 2/2000 | Ohno et al. | 528/170 |

FOREIGN PATENT DOCUMENTS

| FR | 2 302 301 | 9/1976 |
| FR | 2 303 802 | 10/1976 |
| FR | 2 380 732 | 9/1978 |
| FR | 2 434 156 | 3/1980 |
| GB | 2 150 740 | 7/1985 |
| JP | 11-35662 | * 2/1999 |
| WO | WO 95 21871 | 8/1995 |
| WO | WO 99 40025 | 8/1999 |

OTHER PUBLICATIONS

Sawa, N et al. "Quaternary Imidazolium compounds," Chemical Abstacts, vol. 70 (1969), XP-002169538.*

AN:a998:483689 CAPLUS abstract of Golding et al, "Imidazolium room temperature molten salt systems," Molten Salt Forum (1998), Trans Tech Publications Ltd., pp. 589-592.*

AN: 1999:342872 CAPLUS, abstract of McEwen, Alan B. et al, "Electrochemical properties of imidazolium salt electrolytes for electrochemical capacitor applications," Journal of the Electrochemical Society, 1999.*

Chemical Abstracts, vol. 70, No. 3, Jan. 20, 1969 Columbus, Ohio, US; abstract No. 11699f, Sawa Natsuo et al.: "Quaternary imidazolium compounds." XP002169536 abstract-& Database Chemical Abstracts 'Online! CA 70:11699. XP002169538 compounds with RN 21054-86-4, -78-4, -79-5 and -82-0 & JP 06 812354 A (Toho Rayon Co., Ltd.).

Chemical Abstracts, vol. 130, No. 15, Apr. 12, 1999 Columbus, Ohio, US; abstract No. 197145h, Goto, Kenichi et al.: "Lactic acid and its oligomers, high-molecular-weight poly (lactic acid), and high-efficiency manufacture.", XP002169537, abstract -& Database Chemical Abstract 'Online! CA-130:197145, XP002169539 compounds with RN 125376-11-6 and its use as a catalyst & JP 01 135662 A (Mitsui Chemicals Inc.).

"Quaternary imidazolium compounds", Sawa N; Yasuda M, Toho Rayon Co., Ltd, XP-002169538.

Lactic acid and its oligomers, high-molecular-weight poly(lactic acid), and high-efficiency manufacture, K. Goto et al., Mitsui Chemicals Inc., Japan, XP-002169539.

Bonhote, Pierre et al., Hydrophobic, Highly Conductive Ambient-Temperature Molten Salts, Inorganic Chemistry, 1996, 35(5), 1168-1178.

Dai Sheng et al., Solvent Extraction of Strontium Nitrate by a Crown Ether using Room-Temperature Ionic Liquids, Journal of the Chemical Society, 1999, 8, 1201-1202.

Ngo. H.L. et al., Thermal Properties of Imidazolium Ionic Liquids, Thermochimica Acta, 2000, vol. 357-358, 97-102.

* cited by examiner

*Primary Examiner* — Joseph K. McKane
*Assistant Examiner* — Janet L Coppins
(74) *Attorney, Agent, or Firm* — Young & Thompson

(57) ABSTRACT

New 1,2,3- or 1,2,3,4- or 1,2,3,4,5- substituted imidazolium salts and their uses as solvent in catalyzed organic reactions, as well as compositions containing them and a transition metal compound. They can be used in the following reactions: the telomerisation of conjugated dienes, dimerisation of olefins, the oligomerisation of olefins, polymerization of olefins, alkylation of olefins, hydrogenation of olefins, olefin metathesis, hydroformylation of olefins, ring-closing metathesis of olefins, ring-opening metathesis polymerisation of olefins, symetric or asymetric epoxidation of olefins (including heteroatom substituted olefins) and the cyclopropanation of olefins, condensation reaction, hydrogenation reaction, isomerization reaction, Suzuki cross-coupling reactions, amination reaction, partial oxidation of alkanes, kinetic resolution of racemic mixtures, hydrogenation of imines, hydrogenation of ketones, transfer hydrogenation and hydroxylation of aromatic organic compounds.

17 Claims, 2 Drawing Sheets

IMIDAZOLIUM SALTS AND THEIR USE OF THESE IONIC LIQUIDS AS A SOLVENT

The present invention relates to the use of imidazolium salts as solvents and to new imidazolium salts and compositions containing the same. In particular the imidazolium salts may be used as a solvent in organic reactions, in particular in catalytic reactions such as two-phase catalytic conversions of olefins.

Low melting salts, which are liquid at room temperature up to 200° C., can be used as liquid media in many organic reactions. Usually these salts are referred to as "ionic liquids". Frequently the ionic liquids have two functions in that they not only serve as a solvent for the reaction but also as a catalyst or catalyst component.

In other cases the ionic liquids serve only as a solvent for the catalyst, that is the ionic liquid is not miscible with the reactants or the reaction product. In this case the reaction occurs at the phase boundary of the catalyst solution and the reaction products form a separate phase. This process using two separate liquid phases is suitable, if the reaction product must be quickly removed from the reaction mixture in order to avoid subsequent reactions. Moreover the catalyst and the reaction product can be separated under gentle conditions.

Further advantages of ionic liquids are their chemical and thermal stability, which allows their application in many processes. Further they are not volatile and therefore they are safer for chemical industry personnel and the general public and environment.

Among the ionic liquids known as solvents in the art imidazolium salts have attracted attention (for a recent review, see as an example "Ionic liquids" by J. D. Holbrey and K. R. Seddon in *Clean Products and Processes*, 1, (1999), 223-236).

For example *CHEMTECH*, (September 1995), pages 26 and following pages discloses a mixture of 1,3-dialkylimidazolium chloride, in particular 1-n-butyl-3-methyl-imidazolium chloride (abbreviated as BMI$^+$Cl$^-$) and aluminium chloride and/or ethyl aluminium chloride as non-aqueous solvent for the catalyst.

*Am. Chem. Soc., Div. Pet. Chem.*, (1992), 37 pages 370 sqq. discloses the dimerisation of propene in the presence of a solution of NiCl$_2$.(PR$_3$)$_2$, (R=i-C$_3$H$_7$) in a mixture of BMI$^+$Cl$^-$ and AlCl$_3$ as ionic liquid.

EP-A-0 776 880 (corresponding to U.S. Pat. No. 5,874,638) discloses for example a process for the hydroformylation of olefinic compounds in the presence of an ionic liquid.

*Angew. Chem.*, (1995), 107(23/24), pages 2941 sqq. also discloses the hydroformylation reaction using liquid 1,3-dialkylimidazolium salts.

British patent application GB-A-2 150 740, as well as EP-A-0 404 179 and EP-A-0 398 358 disclose 1,2,3-trialkylimidazolium halides and their mixtures with aluminium halides as electrolytes. WO 99/40025 also discloses quaternary onium salts useful as electrolytic solutes. Still other heterocyclic onium salts may be for example used in non-aqueous batteries as disclosed in U.S. Pat. No. 5,827,602 and U.S. Pat. No. 5,683,832.

Other uses of quaternary imidazolium salts are also known, for example as microbicides or plant growth regulators in FR-A-2 434 156, FR-A-2 380 732, FR-A-2 302 301 and FR-A-2 303 802, and as anti-static agents for synthetic fibres in JP 06 812354.

Haloiminium salts (e.g. tri-substituted imidazolium chloride) have been reported as being useful for lactic acid polymerisation (see JP 01 135662). WO 95/21871 presents disubstituted imidazolium halides as catalysts in olefinic polymerisation reactions.

German patent application no. 199 19 494.7 (corresponding to international patent application WO 00/66597) discloses non aqueous ionic ligand liquids of the formula $(Q_1^+)_b A^{tc-}$, wherein $Q_1^+$ is a singly charged ammonium cation, optionally substituted with organic group(s), or the equivalent of a multiply charged ammonium cation and $A^{tc-}$ is an anion of a sulphonated or carboxylated triester of phosphorous acid and c is an integer of at least one. Among the ammonium cations there are also mentioned 1,2,3,4,5-pentamethylimidazolium, 1,2,3,5-tetramethyl-4H-imidazolium, 1,2,3,4-tetramethyl-5H-imidazolium, and 1-trimethylsilyl-2,3,5-trimethyl-4H-imidazolium.

J. Dupont et al. (*Organometallics*, (1998), 17, 815-819) disclose a catalytic process of hydrodimerisation of 1,3-butadiene using palladium compounds dissolved in ionic liquids. As palladium catalyst compounds $[(\eta^3-C_4H_7)Pd-\mu-Cl]_2$, $[(\eta^3-C_4H_7)Pd(1,5-cyclooctadiene)][BF_4]$ and palladium acetate have been used which are told not to be completely soluble and stable in the ionic liquids 1-n-butylmethylimidazolium tetrafluoroborate (BMI$^+$.BF$_4^-$) and 1-n-butylmethylimidazolium hexafluorophosphate (BMI$^+$.PF$_6^-$) at room temperature. At the end of the performed hydrodimerisation reactions however, metallic palladium was detected thus limiting the reutilisation of the catalytic system. This has been attributed to the instability of these catalysts to water. The formation of metallic palladium could be suppressed by the use of a new catalyst precursor (BMI)$_2$PdCl$_4$ which has been obtained by reacting PdCl$_2$ with a 2 molar excess of 1-n-butyl-3-methylimidazolium chloride in acetonitrile at reflux temperature. However even for this stable catalyst, conversions reported were low.

In an attempt to use conventional palladium phosphine catalysts in the presence of ionic liquids such as the above mentioned 1-n-butyl-methylimidazolium tetrafluoroborate BMI$^+$.BF$_4$) or 1-ethyl-3-methylimidazolium bis(trifluoromethane-sulphonyl)imide (EMI$^+$.Tf$_2$N$^-$) for the telomerisation of butadiene for example with methanol, the present inventors found surprisingly that the conventional palladium phosphine catalyst system in the presence of ionic 1,3-dialkylimidazolium liquids in contrast to the above mentioned catalyst compounds like $[(\eta^3-C_4H_7)Pd-\mu-Cl]_2$, $[(\eta-C_4H_7)Pd(1,5-cyclooctadiene)][BF_4]$ or palladium acetate shows almost no reactivity, and thus was not available for a telomerisation process in the presence of the ionic liquid.

Therefore, the object underlying the present invention was to find new stable imidazolium salts which can be used, in particular, in catalytic processes without having a detrimental effect on the catalytic process. Surprisingly the applicant found that imidazolium salts wherein at least the 1,2 and 3-position of the imidazolium heterocycle are substituted have a less detrimental effect when used as a solvent and therefore could be advantageously used as a solvent in catalysed reactions, for example in the catalytic telomerisation of conjugated dienes.

Thus in accordance with the present invention there is provided a new use of 1,2,3-substituted imidazolium salts, 1,2,3,4-substituted imidazolium salts or 1,2,3,4,5-substituted imidazolium salts, with the exception of 1,2,3,4,5-pentamethylimidazolium-, 1,2,3,5-tetramethyl-4H-imidazolium-, 1,2,3,4tetramethyl-5H-imidazolium-, and 1-trimethylsilyl-2,3,5-trimethyl-4H-imidazolium-salts with sulphonated or carboxylated triesters of phosphorous acid as anion, as solvent.

Preferred 1,2,3-substituted imidazolium salts, 1,2,3,4-substituted imidazolium salts or 1,2,3,4,5-substituted imidazolium salts are those of the following formula (1):

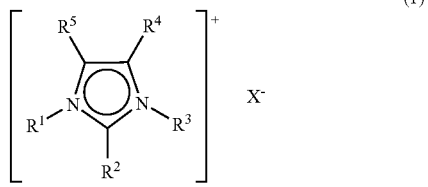

wherein $R^1$ and $R^3$ are the same or different and are each selected from the group consisting of a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms, and a chiral or achiral tri(C1-C10)alkylsilyl group, $R^2$ is selected from the group consisting of a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms and a halogen atom; more preferably $R^2$ is an alkyl group, a cycloalkyl group or an aryl group as defined above, $R^4$ and $R^5$ are the same or different and are each selected from the group consisting of hydrogen, a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms, a chiral or achiral tri(C1-C10)alkylsilyl group, and a halogen atom; more preferably $R^4$ and $R^5$ are hydrogen, an alkyl group, a cycloalkyl group, an aryl group, or a tri(C1-C10)alkylsilyl group, still more preferably hydrogen, and $X^-$ represents an anion.

By "chiral or achiral" is meant groups that may eventually possess one or more chiral centres resulting in an optical activity and/or groups that have an intrinsic optical activity.

The aforementioned alkyl group having up to 10 carbon atoms (sometimes abbreviated as "C1-C10"), preferably up to 6 carbon atoms (sometimes abbreviated as "C1-C6") in the definitions of $R^1$ to $R^5$ includes optionally substituted linear or branched alkyl groups, such as methyl, ethyl, n-propyl, isopropyl, n-butyl, iso-butyl, sec-butyl, tert-butyl, n-pentyl, iso-pentyl, neo-pentyl, n-hexyl, n-heptyl, n-octyl, n-nonyl and n-decyl. Alkyl groups may be substituted by one or more substituents, identical or different. Among these, preferred substituents are halogen atoms. Preferred are alkyl groups with up to 6-carbon atoms, e.g. methyl, ethyl, propyl, isopropyl, butyl, sec-butyl, iso-butyl, tert-butyl, 1-pentyl, 2-pentyl, 3-pentyl, iso-amyl, n-hexyl and iso-hexyl. Preferred substituted alkyl are haloalklyy and perhaloalkyl, e.g. trifluoromethyl, 1,1,1-trifluoroethyl, perfluoroethyl, perfluoropropyl, 1,1,1,2,2,3,3-heptafluorobutyl and perfluorobutyl.

The aforementioned cycloalkyl group of 6 to 10 carbon atoms includes for example cyclobutyl, cyclopentyl, cyclohexyl, cycloheptyl, and cyclo-octyl, as well as bicycloalkyl groups, e.g. bicyclo[3.3.0]octyl, bicyclo[4.3.0]nonyl, bicyclo[4.4.0]decyl and bicyclo[2.2.1]heptyl. Tricycloakyl groups, for example adamantyl, are included in the definition of cycloalkyl and are also part of the present invention. Cycloalkyl groups may be substituted by one or more identical or different substituents chosen, for example, from among alkyl groups and halogen atoms.

The aforementioned aryl group of 6 to 10 carbon atoms includes for example phenyl or naphthyl. Aryl groups may bear one or more substituents, identical or different.

The skilled artisan will appreciate that all various substituents on the alkyl, cycloalkyl and/or aryl groups are all identical or different and, when present, serve to the formation of tri-, tetra-, and penta-substituted imidazolium salts, the use of which being one of the purposes of the present invention.

With respect to the above mentioned (C1-C6)alkyl moiety of the tri(C1-C6)alkylsilyl group it is referred to the definition of the (C1-C6)alkyl groups for $R^1$ to $R^5$.

Halogen atoms in the above definitions include for example fluorine, chlorine, bromine and iodide.

In the above formula (1), $X^-$ anion represents any anion known by the skilled artisan.

Preferred anions $X^-$ in the above mentioned formula (I) are preferably selected from, but not limited to, anions of the group consisting of fluoride, chloride, bromide, iodide, hexafluorophosphate, hexafluoroantimonate, hexafluoroarsenate, fluorosulphonate, tetrafluoroborate, bis-perfluoro(C1-C10)alkylsulphonyl amides, perfluoro(C1-C10)alkyl sulphonates, dichlorocuprate, tetrachloroborate, tetrachloroaluminate, heptachlorodialuminate ($Al_2Cl_7^-$), trichlorozincate, and anions of sulphonated or carboxylated (alkyl, cycloalkyl and/or aryl)-phosphines or -phosphites.

Particularly preferred anions in the above formula (1) are those selected from fluoride, chloride, bromide, iodide, hexafluorophosphate, fluorosulphonate, tetrachloroborate, tetrafluoroborate, bis-perfluoro(C1-C10)alkylsulphonyl amides, perfluoro(C1-C10)alkyl sulphonates, and anions of sulphonated or carboxylated (alkyl, cycloalkyl and/or aryl)-phosphines or -phosphites.

With respect to the aforementioned (C1-C10)alkyl moiety in the definitions "bis-perfluoro(C1-C10)alkylsulphonyl amide" and "perfluoro(C1-C10)alkyl sulphonate" it is referred to the definition of the C1-C10 alkyl groups for $R^1$ to $R^5$ above.

Preferred imidazolium salts of formula (1) used as solvents are those having the following characteristics taken alone or in combination:

$R^1$, $R^2$ and $R^3$, identical or different, are each independently chosen from (C1-C6)alkyl, (C1-C6)haloalkyl and cycloalkyl;

$R^4$ and $R^5$, identical or different, are each independently chosen from hydrogen, (C1-C6)alkyl, (C1-C6)haloalkyl and cycloalkyl;

and $X^-$ represents an anion as hereinbefore described.

Most preferred imidazolium salts of formula (1) used as solvents have the following characteristics taken alone or in combination:

$R^1$, $R^2$ and $R^3$, identical or different, are each independently chosen from methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;

$R^4$ and $R^5$, identical or different, are each independently chosen from hydrogen, methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;

and $X^-$ represents an anion as hereinbefore described.

Particular preferred solvents are 1,2,3-tri(C1-C10)alkylimidazolium salts. With respect to the aforementioned (C1-

C10)alkyl moiety in the "1,2,3-tri(C1-C10)-alkyl-imidazolium salts" it is referred to the definition of the C1-C10 alkyl groups for $R^1$ to $R^5$ above.

(Alkyl, cycloalkyl and/or aryl)-phosphines or phosphites in the definition of the anions of sulphonated or carboxylated (alkyl, cycloalkyl and/or aryl)-phosphines or phosphites include all kinds of anions of alkyl and aryl phosphines or phosphites like monodentate or bidendate phosphines or phosphites having up to 36 carbon atoms in the hydrocarbon moieties, like alkyl, aryl arylalkyl, cycloalkyl, cycloalkylalkyl, etc.

Especially preferred salts of formula (1) used as solvents include 1-ethyl-2,3-dimethylimidazolium bromide ([EMMI][Br]), 1-ethyl-2,3-dimethylimidazolium bistrifluoromethylsulphonylamide ([EMMI][Tf$_2$N]), 1-ethyl-2,3-dimethylimidazolium trifluoromethylsulphonate ([EMMI][CF$_3$SO$_3$]), 1-n-butyl-2,3-dimethylimidazolium chloride ([BMMI][Cl]), 1-n-butyl-2,3-dimethylimidazolium hexafluorophosphate ([BMMI][PF$_6$]), 1-n-butyl-2,3-dimethylimidazolium bistrifluoromethylsulphonylamide ([BMMI][Tf$_2$N]), and 1-n-butyl-2,3-methylimidazolium tetrafluoroborate ([BMMI][BF$_4$]).

In a particular preferred embodiment, 1-n-butyl-2,3-dimethylimidazolium salt is used as a solvent, and more specifically 1-n-butyl-2,3-dimethylimidazolium chloride, 1-n-butyl-2,3-dimethylimidazolium hexafluorophosphate, 1-n-butyl-2,3-dimethylimidazolium bistrifluoromethylsulphonylamide and/or 1-n-butyl-2,3-methylimidazolium tetrafluoroborate are used as solvents.

Preferably the above substituted imidazolium salts are used as a solvent in organic reactions, in particular in the presence of a catalyst, wherein the catalyst may comprise a transition metal compound, in particular from the group VIIIB of the periodic system of elements.

Preferably the above substituted imidazolium salts are used as a solvent in organic reactions, selected from the group consisting of the catalytic conversion of olefins selected from the telomerisation of conjugated dienes, the dimerisation of olefins, the oligomerisation of olefins, the polymerisation of olefins, the alkylation of olefins, the hydrogenation of olefins, the olefin metathesis, the hydroformylation of olefins, the ring-closing metathesis of olefins, the ring-opening metathesis polymerisation of olefins, the symmetric or asymmetric epoxidation of olefins (including heteroatom substituted olefins) and the cyclopropanation of olefins, the condensation reaction, the hydrogenation of, in particular, aldehydes, the isomerisation reaction, the Suzuki cross-coupling reactions, the amination reaction, the partial oxidation of alkanes, the kinetic resolution of racemic mixtures, the hydrogenation of imines, the hydrogenation of ketones, the transfer hydrogenation, and the hydroxylation of aromatic organic compounds.

Preferred reactions, wherein the solvent is an imidazolium salt of formula (1), are reactions of catalytic conversion of olefins.

A particular preferred process is the telomerisation of conjugated dienes.

In some cases the 1,2,3-susbtituted imidazolium salts, 1,2,3,4-substituted imidazolium salts or 1,2,3,4,5-substituted imidazolium salts, or mixtures thereof, with the exception of 1,2,3,4,5-pentamethyl imidazolium-, 1,2,3,5-tetramethyl-4H-imidazolium-, 1,2,3,4-tetramethyl-5H-imidazolium-, and 1-trimethylsilyl-2,3,5-trimethyl-4H-imidazolium-salts with sulphonated or carboxylated triesters of phosphorous acid as anion, act also as a catalyst, and accordingly, the present invention is also related to the use of the above imidazolium salts as a catalyst or catalyst component, in particular in transition metal catalyst systems. This is particularly true in those cases where the anion of the imidazolium salt is a phosphorous containing anion like anions of the aforementioned sulphonated or carboxylated (alkyl and/or aryl) phosphines or phosphites.

Such anions are disclosed for example in EP-A-0 924 218 (U.S. Pat. No. 6,103,908) and shall be included within the scope of the present invention. EP-A-0 924 218 discloses nonaqueous ionic ligand liquids of the formula $(Q^+)_a A^{a-}$, wherein $Q^+$ is a singly charged quaternary ammonium and/or phosphonium cation or the equivalent of a multiply charged ammonium and/or phosphonium cation and $A^{1-}$ is a triarylphosphine anion of the formula:

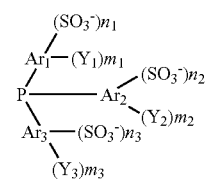

where $Ar_1$, $Ar_2$ and $Ar_3$ are individually aryl of 6 to 14 carbon atoms, the substituents $Y_1$, $Y_2$ and $Y_3$ are individually selected from the group consisting of alkyl and alkoxy of 1 to 4 carbon atoms, chlorine, bromine, hydroxyl, cyano, nitro and amino groups of the formula $NR^6R^7$, where $R^6$ and $R^7$ are individually hydrogen or alkyl of 1 to 4 carbon atoms, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1, and a is $n_1+n_2+n_3$, and amines and/or phosphines derived from $Q^+$ are present in an excess of up to 5 equivalents over the stoichiometrically required amount for the formation of $(Q^+)_a A^{a-}$ or alkali metal or alkaline earth metal salts of the triarylphosphines $A^{a-}$ are present in an excess of up to 5 equivalents over the stoichiometrically required amount for the formation of $(Q^+)_a A^{a-}$.

Similarly the above mentioned German patent application no. 19919494.7 (corresponding to international patent application no. WO 00/66597) discloses suitable non-aqueous ionic ligand liquids of the formula $(Q_1^+)_b A^{\prime b-}$, wherein $Q_1^+$ is a singly charged ammonium cation, optionally substituted with organic group(s), or the equivalent of a multiply charged ammonium cation and $A^{\prime b-}$ is an anion of a sulphonated or carboxylated triester of phosphorous acid and b is an integer of at least one. These ammonium salts of sulphonated or carboxylated phosphorous acids may be formally derived from phosphorous acid by esterification with the ammonium salts of hydroxysulphonic acids or hydroxycarboxylic acids of the following general formula (Qac)$_c$-Y—(OH)$_d$, wherein ac is the acid residue, namely the sulphonic acid residue —SO$_3^-$, 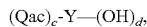 and the carboxylic acid residue, respectively and Q is as already mentioned a singly charged ammonium cation, optionally substituted with organic group(s), or the equivalent of a multiply charged ammonium cation, Y represents an organic residue and is preferably a branched or non-branched saturated aliphatic hydrocarbon group having a total of up to 20 carbon atoms, optionally substituted by hydroxy or C1-C10 alkoxy, c and d are integers of at least 1, d is preferably 1 or 2. Also these anions of sulphonated or carboxylated phosphoric acids, in particular sulphonated aryl or caraboxylated aryl phosphorous acids may be used as anions of the imidazolium cations in accordance with the present invention.

Further the present invention relates to the use of the above mentioned 1,2,3-substituted imidazolium salts, 1,2,3,4-substituted imidazolium salts or 1,2,3,4,5-substituted imidazolium salts, or mixtures thereof, with the exception of 1,2,3,4,5-pentamethylimidazolium-, 1,2,3,5-tetramethyl4H-imidazolium-, 1,2,3,4-tetramethyl-5H-imidazolium-, and 1-timethylsilyl-2,3,5-trimethyl-4H-imidazolium-salts with a sulphonated or carboxylated triester of phosphorous acid as anion, in a two-phase catalytic reaction, preferably as solvent and/or catalyst or catalyst component.

The present invention also relates to the use of 1,2,3- and/or 1,2,3,4- and/or 1,2,3,4,5-substituted imidazolium salts, in particular those defined above, with a metal compound catalyst or catalyst component, in particular in organic reactions as defined above. The salts can have a role of solvent and possibly of catalyst or catalyst component, preferably solvent.

The use of salts containing chiral group(s) leading to a chiral solvent may advantageously confer enantioselectivity to the reaction wherein they are used.

Still further the present invention relates to new imidazolium salts of the following formula (1):

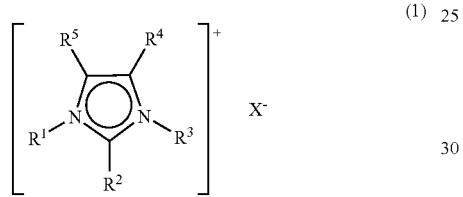

(1)

wherein $R^1$ and $R^3$ are the same or different and are each selected from the group consisting of a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms, and a chiral or achiral tri(C1-C10)alkylsilyl group, $R^2$ is selected from the group consisting of a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms and a halogen atom; more preferably $R^2$ is an alkyl group, a cycloalkyl group or an aryl group as defined above, $R^4$ and $R^5$ are the same or different and are each selected from the group consisting of hydrogen, a chiral or achiral alkyl group having up to 10, preferably up to 6 carbon atoms, a chiral or achiral cycloalkyl group of 4 to 10 carbon atoms, a chiral or achiral aryl group of 6 to 10 carbon atoms, a chiral or achiral tri(C1-C10)alkylsilyl group, and a halogen atom; more preferably $R^4$ and $R^5$ are hydrogen, an alkyl group, a cycloalkyl group, an aryl group, or a tri(C1-C10)alkylsilyl group, still more preferably hydrogen, and $X^-$ represents an anion, with the exception of 1,2,3,4,5-pentamethylimidazolium-, 1,2,3,5-tetramethyl-4H-imidazolium-, 1,2,3,4-tetramethyl-5H-imidazolium, and 1-trimethylsilyl-2,3,5-trimethyl-4H-imidazolium-salts of sulphonated or carboxylated triesters of phosphorous acid, 1,2,3,4,5-pentamethylimidazolium iodide, 1,2,3-trimethylimidazolium bromide, 1,2,3-trimethylimidazolium iodide, 1,2-dimethyl-3-ethylimidazolium bromide, 1,2-dimethyl-3-ethylimidazolium chloride, 1,2-dimethyl-3-butylimidazolium fluoride, 1-butyl-2,3-dimethylimidazolium salt of 2,2'-(2,5-cyclohexadiene-1,4-ylidene) bis[propanedinitrile], 1,3-dimethyl-2,4,5-trichloroimidazolium tetrafluoroborate, 1,3-dimethyl-2,4,5-tribromoimidazolium tetrafluoroborate, 1,3-dimethyl-2,4,5-tribromoimidazolium bromide.

With respect to the explanation of the substituents it is referred to the definitions and preferred definitions given above.

Preferred imidazolium salts according to the invention are those having the following characteristics taken alone or in combination:

$R^1$, $R^2$ and $R^3$, identical or different, are each independently chosen from (C1-C6)alkyl, (C1-C6)haloalkyl and cycloalkyl;

$R^4$ and $R^5$, identical or different, are each independently chosen from hydrogen, (C1-C6)alkyl, (C1-C6)haloalkyl and cycloalkyl;

and $X^-$ represents an anion as hereinbefore described.

Most preferred imidazolium salts of formula (1) have the following characteristics taken alone or in combination:

$R^1$, $R^2$ and $R^3$, identical or different, are each independently chosen from methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;

$R^4$ and $R^5$, identical or different, are each independently chosen from hydrogen, methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;

and $X^-$ represents an anion as hereinbefore described.

Particular preferred salts of the present invention are 1,2,3-tri(C1-C10)alkyl-imidazolium salts. With respect to the aforementioned (C1-C10)alkyl moiety in the "1,2,3-tri(C1-C10)alkyl-imidazolium salts" it is referred to the definition of the C1-C10 alkyl groups for $R^1$ to $R^5$ above.

(Alkyl, cycloalkyl and/or aryl)-phosphines or phosphites in the definition of the anions of sulphonated or carboxylated (alkyl, cycloalkyl and/or aryl)-phosphines or phosphites include all kinds of anions of alkyl and aryl phosphines or phosphites like monodentate or bidendate phosphines or phosphites having up to 36 carbon atoms in the hydrocarbon moieties, like alkyl, aryl, arylalkyl, cycloalkyl, cycloalkylalkyl, etc.

In a preferred embodiment, salts of formula (1) include those wherein $R^1$, $R^2$, $R^3$, $R^4$ and $R^5$ are as described above and $X^-$ is chosen from fluoride ($F^-$), chloride ($Cl^-$), bromide ($Br^-$), iodide ($I^-$), bistrifluoromethylsulphonylamide ($Tf_2N^-$), trifluoromethylsulphonate ($CF_3SO_3^-$), hexafluorophosphate ($PF_6^-$), and tetrafluoroborate ($BF_4^-$).

More specifically, $X^-$ is chosen from bistrifluoromethylsulphonylamide ($Tf_2N^-$), trifluoromethylsulphonate ($CF_3SO_3^-$), hexafluorophosphate ($PF_6^-$), and tetrafluoroborate ($BF_4^-$)

Especially preferred salts of formula (1) used as solvents include 1-ethyl-2,3-dimethylimidazolium bromide ([EMMI][Br]), 1-ethyl-2,3-dimethylimidazolium bistrifluoromethylsulphonylamide ([EMMI][Tf$_2$N]), 1-ethyl-2,3-dimethylimidazolium trifluoromethylsulphonate ([EMMI][CF$_3$SO$_3$]), 1-n-butyl-2,3-dimethylimidazolium chloride ([BMMI][Cl]), 1-n-butyl-2,3-dimethylimidazolium hexafluorophosphate ([BMMI][PF$_6$]), 1-n-butyl-2,3-dimethylimidazolium bistrifluoromethylsulphonylamide ([BMMI][Tf$_2$N]), and 1-n-butyl-2,3-methylimidazolium tetrafluoroborate ([BMMI][BF$_4$]).

Particular preferred imidazolium salts of the invention are 1-n-butyl-2,3-dimethylimidazolium bistrifluoro(C1-C10, preferably C1 (methyl))alkylsulphonylamide, 1-n-butyl-2,3- dimethylimidazolium tetrafluoroborate and 1-n-butyl-2,3-dimethylimidazolium hexafluorophosphate.

The present invention also concerns compositions or mixtures comprising at least one 1,2,3- or 1,2,3,4- or 1,2,3,4,5-substituted imidazolium salt, in particular as defined above, as a solvent; and at least one transition metal or at least one catayst, in particular a catalyst comprising a transition metal compound; transition metal may be in particular from group VIIIB, e.g. as further defined herein. The catalyst can be any catalyst usually used in the catalytic reactions defined above. The composition may also comprise the reactant(s).

These compositions or mixtures may comprise salts as defined above with the specified both kind of exceptions.

Such compositions or mixtures may also comprise a phosphorous-containing compound as defined hereinafter.

The amount of these phosphorus-containing compounds is in general from 0.01 to 100, preferably from 1 to 20, in particular from 1 to 5 mole per mole of the transition metal.

The concentration of the transition metal is usually in the range of 1 to 200 mM per liter of ionic liquid and more preferably 10 to 50.

The amount of the salt in the reaction system is usually 5 to 100 parts per 100 parts of the reactant(s), e.g. diolefin, preferably 10 to 50.

Usually the imidazolium salts have a melting point of below 200° C., preferably below 160° C., more preferably below 140° C., still more preferably below 120° C., and most preferably below 100° C., in particular, below 90° C. (the melting points are measured at normal pressure with a digital apparatus such as of Electrothermal).

1-n-Butyl-2,3-dimethylimidazolium chloride (BMMI$^+$ Cl$^-$) has a melting point of 104-105° C., 1-n butyl-2,3-dimethylimidazolium bistrifluoromethylsulphonylanide (BMMI$^+$Tf$_2$N$^-$), and 1-n-butyl-2,3-dimethylimidazolium tetrafluoroborate (BMMI$^+$BF$_4^-$) are liquids at room temperature.

Synthesis of non aqueous ionic liquids based on unsymmetrical substituted 1,2,3-trialkylimidazolium can be performed following two main schemes. According to the first one, the N-alkylimidazole or 1,2-dialkylimidazole (generally commercial products) are alkylated with an organic halide and the desired salt is then obtained by anion exchange reactions (metathesis). According to the second one, the liquid is obtained directly by the quaternisation of an N-alkylimidazole, with the alkylating agent itself providing a suitable anion.

For the indirect route (1) one can refer to P. Bonhôte, A.-P. Dias, N. Papageorgiou, K. Kalyanasundaram, Gratzel, M. Inorg. Chem., (1996), 35, 1168-1178; J. S. Wilkes, M. J. Zaworrotko, J Chem. Soc., Chem. Commun., (1992), 965-967; J. Fuller, R. T. Carlin, R. A. Osteryoung, J. Electrochem. Soc., (1997), 144, 3881-3886. Generally, bromide or chloride imidazolium can be used as intermediate in the synthesis of the final ionic liquid. The anion exchange involved in the second step can be performed in different solvents: water (see J. D. Holbrey, K. R. Seddon, J. Chem. Soc., Dalton Trans., (1999), 2133-2139) or acetone (see P. A. Suarez, J. E. L. Dullius, S. Einloft, R. F. de Souza, J. Dupont, Polyhedron, (1996), 15, 1217-1219 and P. A. Suarez, S. Einloft, J. E. L. Dullius, R. F. de Souza, J. Dupont, J. Chim. Phys., (1998), 95, 1626-1639).

The direct synthesis route (2) allows one to obtain an ionic liquid without any addition of halide by the reaction of an N-alkylimidazole with an appropriate alkylating agent. The alkylating agent must be able to realise both the quaternisation of the imidazole ring and the introduction of a non-coordinating anion. Can be used among others, alkylating agents derived from alkyltriflates (methyl and ethyltriflate) (see P. Bonhôte, A.-P. Dias, N. Papageorgiou, K. Kalyanasundaram, Gratzel, M. Inorg Chem., (1996), 35, 1168-1178). Reaction is carried out in refluxing 1,1,1-trichloroethane, a solvent chosen for its stability toward strongly allkylating agents and the insolubility of the imidazolium salts in this milieu. To prevent alkyltriflate hydrolysis the reaction must be conducted under dry argon. Nearly quantitative yields were obtained.

The syntheses of [R$^1$R$^2$I][BF$_4$] and [R$^1$R$^2$I][PF$_6$] salts can be prepared using the first route which involves metathesis reaction from the corresponding chloride or bromide salts with NaBF$_4$ and NaPF$_6$ in water (see J. D. Holbrey, K. R Seddon, J. Chem. Soc., Dalton Trans., (1999), 2133-2139), methanol (see J. S. Wilkes, M. J. Zaworrotko, J. Chem. Soc., Chem. Commun., (1992), 965-967), or acetone (see P. A. Suarez, J. E. L. Dullius, S. Einloft, R. F. de Souza, J. Dupont, Polyhedron, (1996), 15, 1217-1219). They can also be obtained by using other alkylating agents. Those are triethyloxonium tetrafluoroborate and triethyloxonium hexafluorophosphate. As with ethyltriflate, the oxonium salt [Et$_3$O][BF$_4$] reacts with one equivalent of 1-alkylimidazole (or 1,2-dialkyimidazole) in refluxing methylene dichloride with very high yields (see patent application by H. Olivier, F. Favre., IFP, no. FR 2.779.143, (1998)). All prepared imidazolium ionic liquids were air stable under ambient conditions and may be handled under normal laboratory conditions.

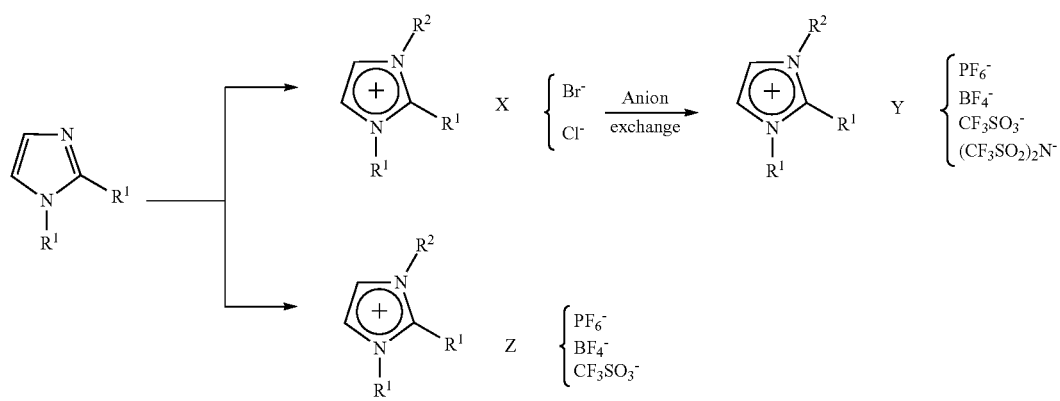

The use of the present invention is now exemplified further in a process for telomerising conjugated dienes.

The catalytic dimerisation of dienes under the concomitant addition of a nucleophilic reagent was reported simultaneously in 1967 by Smutny at Shell and Takahashi at Osaka University. The reaction is defined under the general term of telomerisation as the dimerisation of two conjugate diolefins (telomers) together with the addition of a third molecule (telogen) over one double bond equivalent.

Usually the process for telomerising a conjugated diene is carried out in the presence of a transition metal compound and a phosphorus-containing compound.

The conjugated diene preferably has 4 to 6 carbon atoms. Particularly preferred the conjugated diene is selected from butadiene, isoprepene or 1,3-pentadiene. The most preferred conjugated diene is butadiene.

Telogens can be for example compounds containing active hydrogen, preferably a compound of the general formula

H-A wherein A is selected from the group consisting of hydroxy, alkoxy, cycloalkoxy, hydroalkoxy, alkenyloxy, aryloxy, alkanoloxy, mono- or dialkylamino, tri(alkyl- and/or aryl)silyl, and an alkyl group substituted in the α-position with at least one electron attracting group, preferably selected from alkoxycarbonyl, alkanoyl and/or cyano, wherein the above mentioned alkyl moieties independently from each other are branched or linear and each may have up to 8 carbon atoms, and wherein the above mentioned aryl moieties independently from each other may have up to 10 carbon atoms.

Thus the compound containing active hydrogen includes for example water, alkanols like methanol, ethanol, n-propanol, iso-propanol, n-butanol, iso-butanol, sec-butanol etc., cycloalkanols like cyclohexanol etc., alkandiols like glycol, triethyleneglycol, polyethylene glycol, 1,2- or 1,3-propandiol etc., alkenols like allyl alcohol etc., aromatic alcohols like phenols, naphtols etc., carboxylic acids like acetic acid etc., amines like primary or secondary amines like methyl amine, ethyl amine, dimethyl amine, diethyl amine etc., tri(alkyl- and/or aryl) silanes, like trimethyl silane, triethyl silane, triphenyl silane, phenyl dimethyl silane etc., and CH-acidic compounds with activated methylene groups (so-called "Michael-Donors") like malonic acid dialkyl esters, acetic acid alkyl esters etc.

Particularly preferred telogens are water, methanol and glycol, and the most preferred is methanol.

The transition metal compound can be any transition metal compound suitable for catalysis of the telomerisation reaction in the presence of the phosphorous compound and the salt. Preferably it is a compound of an element of the group VIIIB (or 8, 9 and 10) of the periodic system of elements, that is a compound selected from iron, cobalt, nickel, ruthenium, rhodium, palladium, osmium, iridium and platinum. More preferred compounds are selected from compounds such as cobalt, rhodium, nickel, platinum and platinum. Concerning possible transition metal compounds for carrying out the telomerisation process, reference is made to A. Behr in "Aspect of Homogeneous Catalysis, A series of Advances"; Edited by R. Ugo; D. Reidel Publishing Company; Vol. 5; pp. 3-73, (1984) -Tsuji, *J. Adv. Organomet. Chem.*, (1979), 17, 141-W. Keim, "*Transition Metals in Homogeneous Catalysis*", Ed. G. N. Schrauzer, p. 59, Marcel Dekker, New York, (1971)-R. Baker, *Chem. Rev.,* 73, 487, (1973)-P. N. Rylander, "Organic Chernistry", vol. 28, p 175, Academic Press, New York, (1973).

Most preferred are palladium compounds, for example, known palladium compounds used in telomerisation processes for example those described in U.S. Pat. Nos. 5,043, 487, 4,356,333, 4,142,060, EP-A-0 436 226, WO 98/08794, WO 96/30636 and U.S. Pat. No. 4,417,079 the relevant content of which is herein incorporated by reference.

Examples of these palladium compounds include soluble palladium(0) and palladium(II) compounds, for example, palladium acetylacetonate, π-allylpalladium acetate, π-allylpalladium chloride, palladium acetate, palladium carbonate, palladium nitrate, palladium chloride, sodium chloropalladate, bis(benzonitrile)palladium chloride, bis (triphenylphosphine)palladium chloride, bis (triphenylphosphine)-palladium acetate, bis(1,5-cyclooctadiene)palladium and bis(π-allyl)palladium.

A particular preferred palladium compound is palladium acetate ($Pd(OAc)_2$).

The active species of the transition metal compound is a low-valence transition metal complex which may be formed by reduction in. the presence of butadiene or by suitable reducing agents added.

The transition metal compound can be present in the reaction system in any optional amount but, from the standpoint of commercial production, the transition metal compound is preferably present in such an amount as to assure the concentration of transition metal atom of 0.1 to 50 mg atoms, more preferably 0.5 to 5 mg atoms per liter of the reaction mixture.

The ratio of the transition metal compound to the conjugated diene is not critical, but is preferably from $10^{-5}$ to $10^{-1}$, in particular from $10^{-4}$ to $10^{-2}$ mole of the transition metal per mole of the conjugated diene.

The phosphorus-containing compound which forms part of the catalyst system is not particularly restricted but can be any phosphorus-containing compound, capable of coordinating to the transition metal compound, for example hydrophobic or hydrophilic, water-soluble, mono- or bidentate phosphorus-containing compounds known for telomerisation processes (e.g. those known from U.S. Pat. Nos. 5,043,487, 5,345,007, 4,356,333, EP-A-0 436 226, WO 98/08794, WO 95/30636, U.S. Pat. Nos. 4,417,079 and 4,142,060 the relevant content of which is herein incorporated by reference).

Suitable examples include phosphines or phosphites, preferably mono- or bidentate alkylphosphines, arylphosphines, arylalkyphosphines, alkylphosphites, arylphosphites, and arylalkyphosphites, wherein the hydrocarbon moieties may each independently have up to 36 carbon atoms, preferably 24 carbon atoms, more preferably 10 carbon atoms and may be substituted by one of three suitable substituents preferably selected from a sulphonic acid group or a salt thereof, a carboxylic acid group or a salt thereof and an allyl group. Salts of the sulphonic acid or carboxylic acid group include for example alkali metal salts like sodium or potassium salts and ammonium salts.

Examples of these phosphines or phosphites include tributylphosphine, dimethyl-n-octylphosphine, tricyclohexylphosphine, triphenylphosphine (TPP), tritolylphosphine, tris (para-methoxyphenyl)phosphine, diphenylethylphosphine, dimethylphenylphosphine, 1,2-bis-diphenylphosphinoethane, triethylphosphite, tricyclohexylphosphite and triphenylphosphite, hydrolilic arylphosphines, lilke sulphonated or carboxylated arylphosphines, preferably water-soluble salts of mono-, di- or trisulphonated triphenylphosphine compounds like trisodium tris(meta-sulphonatophenyl)phosphine) (TPPTS), bis(para-sulphonatophenyl)phenylphosphine dihydrate dipotassium salt (TPPDS) and diphenylphosphinobenzene-3-sulphonic acid sodium salt (TPPMS).

In general, the phosphines are preferred to the phosphites since the latter depending on the telogen used may undergo hydrolysis and rearrangement reactions. Particularly preferred are aryl phosphine compounds, sulphonated or not, like the above mentioned TPP, TPPTS, TPPDS and TPPMS.

Such phosphorous-containing compounds can be present in the compositions or mixtures defined above without being limited to a telomerisation process.

The amount of these phosphorus-containing compounds is in general from 1 to 100, preferably from 1 to 20, in particular from 1 to 5 mole per mole of the transition metal.

Depending on the telogen, to be telomerised, the phosphorus-containing compound used as the catalyst component and the relative amounts of the reactants in some instances monophasic reaction systems may be formed. These monophasic reaction systems can be usually transferred into biphasic systems by addition of at least one non-polar solvent (usually a solvent which is immiscible with water). Thereby a phase consisting of the solvent and the product (usually the upper phase and a phase consisting of the salt (or ionic liquid) and the major part of catalyst (usually the lower phase) are formed. In some cases, depending on the teloger used and the catalyst system part of the catalyst may be contained also in the product phase. The non-polar solvent may include for example aliphatic hydrocarbons, for example alkanes like pentane, hexane, heptane, and octane etc., cycloalkanes like cyclopentane, cyclohexane etc., aromatic hydrocarbons like benzene, toluene, xylene etc. and aliphatic or aromatic ethers, like diethyl ether, tetrahydrofuran, anisol, methyl-tert-butyl ether (MTBE), diethylene glycol, dimethoxyethane, etc. The present invention includes also the case where the imidazolium salts are used together with such conventional non-polar solvents and/or polar solvents like water. A particular preferred non-polar solvent is n-heptane.

Depending on the telogen the desired products are for example trans- and cis-1-methoxy-2,7-octadiene and 3-methoxy-1,7-octadiene for methanol, cis- and trains-2,7-octadiene-1-ol and 1,7-octadiene-3-ol for water, and cis- and trans-1-hydroxy-2-(2,7-octadienyl-1-oxy)ethane and 1-hydroxy-2-(1,7-octadienyl-3-oxy)ethane for glycol.

The obtained unsaturated products can be hydrogenated catalytically into the corresponding saturated compounds in a known manner.

The telomerisation reaction is usually performed under a pressure of from normal pressure to 200 bar, preferably from normal pressure to 30 bar.

The temperature of the telomerisation reaction is usually in the range of 20 to 200° C. preferably of 30 to 180° C., more preferably of 40 to 140° C. and still more preferably of 40 to 120° C.

The concentration of the transition metal is usually in the range of 1 to 200 mM per liter of ionic liquid and more preferably 10 to 50.

The amount of the salt in the reaction system is usually 5 to 100 parts per 100 parts of the diolefin, preferably 10 to 50.

The molar ratio of telogen/conjugated diolefin is usually in the range 0.5 to 10, preferably 0.5 to 5.

As generally known, the telomerisation of butadiene with water as the telogen is preferably carried out in the presence of a base and under $CO_2$-pressure. Suitable bases include for example the hydroxides of alkali metals and alkaline earth metals and amines. Suitable amines include for example tertiary amines having a basicity constant (pKa) of at least 7, for example tri(C1-C6)alkylamines such as trimethylamine, triethylamine, tri-n-propylamine, tri-n-butylamine, etc.; aminoalcohols such as 1-N,N-dimethylamino-2-propanol, 1-N,N-dimethylamino-3-butanol, etc.; and N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, N,N,N',N'-tetramethyl-1,3-butanediamine and the like. Among these, triethylamine is most preferred.

Further carbonate and/or bicarbonate ions may be present along with the tertiary amine to accelerate the rate of n-octadienol formation. Carbonate and bicarbonate ions are conveniently derived from carbon dioxide, sodium bicarbonate or formic acid, which releases these ions in the reaction system. Among these, carbon dioxide is most preferred.

The amount of carbon dioxide which promotes the butadiene telomerisation is not critical and may range from about $10^{-3}$ to 1, preferably from $10^{-2}$ to 0.5, mol per mole of the conjugated diene.

The substituted 1,2,3-, 1,2,3,4- and 1,2,3,4,5-substituted imidazolium salts of the present invention can be used as a solvent for the hydrodimerisation with rates under the conditions already known.

In the following examples the use according to the present invention is exemplified in the catalytic conversion of conjugated dienes (telomerisation) and oligomerisation of dienes. It is however to be understood that the present invention is not limited to such uses.

EXAMPLES

A—Preparation of Non-aqueous Ionic Liquids a—Materials

Figure 1:
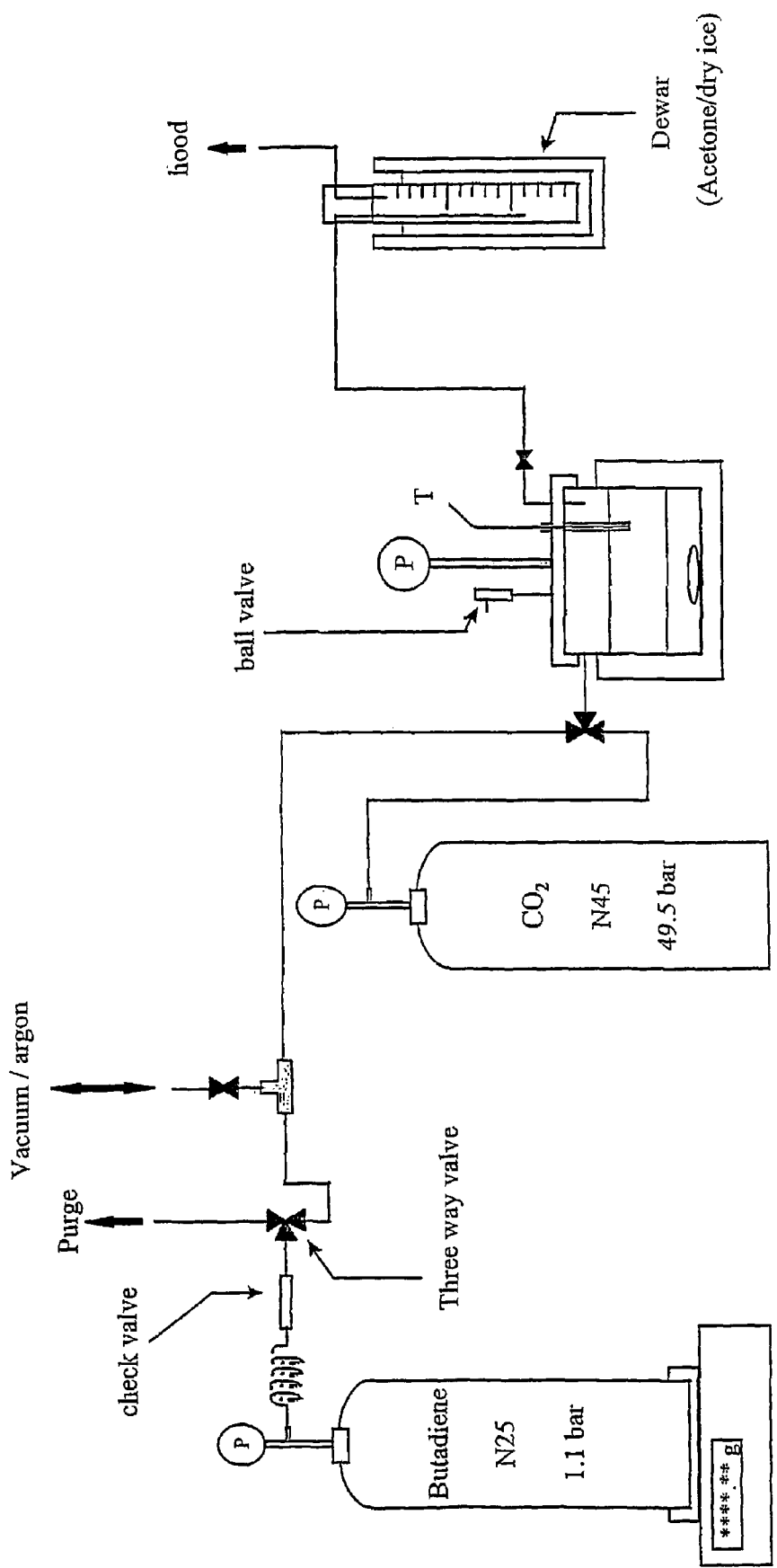
FIG. 1 shows the apparatus for telomerising butadiene which has been used in the examples.
Figure 2:
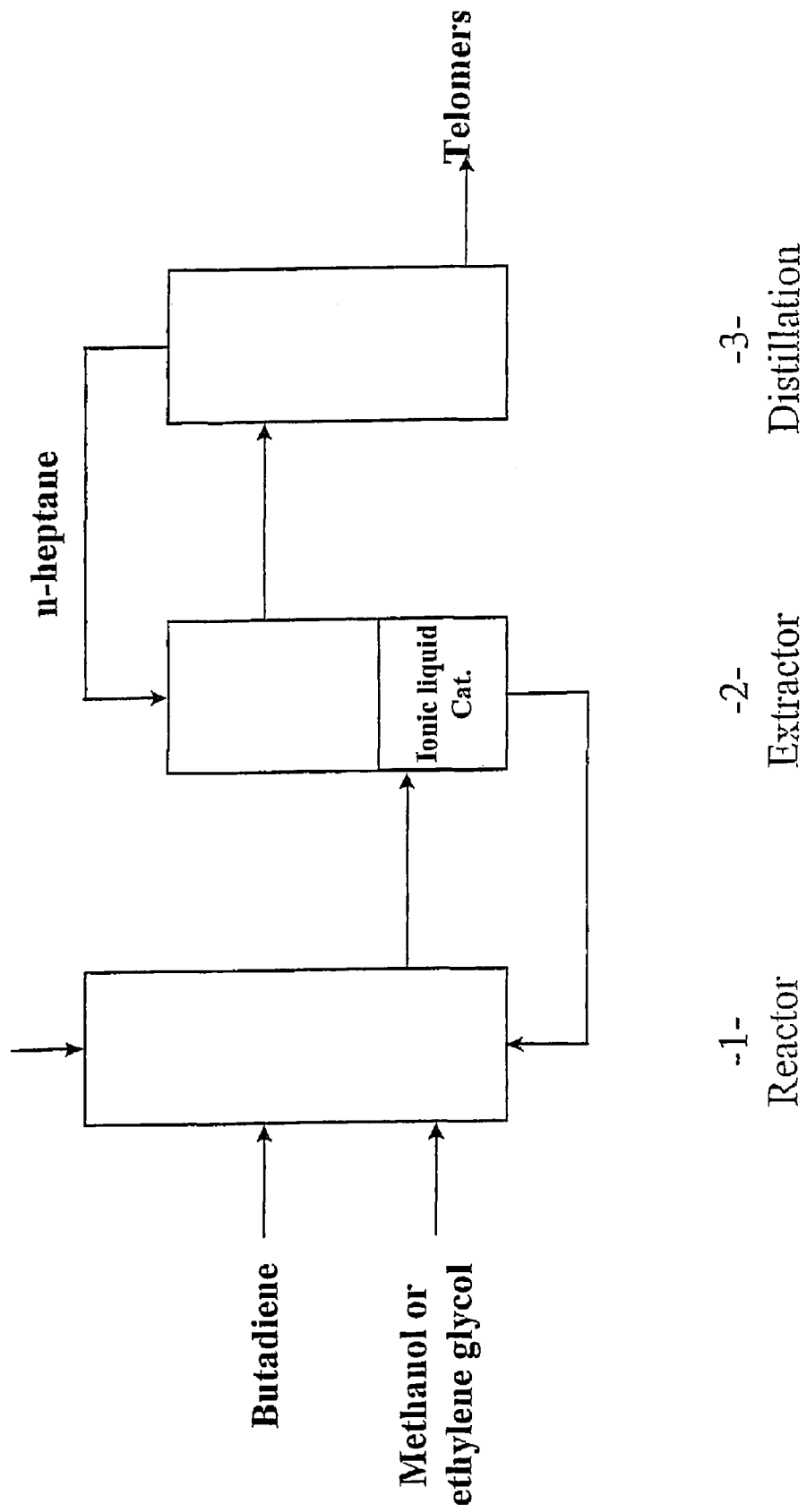
FIG. 2 shows an embodiment of a two-phase process of telomerisation of butadiene ($C_4H_6$) with MeOH or ethylene glycol in the ionic liquids in accordance with the present invention.

All syntheses are carried out under dry argon using standard Schlenk techniques. Methylene dichloride is distilled over $P_2O_5$ and stored over 0.3 nm molecular sieves. All other reagents (1,2-dimethylimidazole, pyridine, $HPF_6$, 1-chlorobutane) are purchased from Aldrich and used as is, unless otherwise indicated.

b—Physicochemical Measurements

Proton and carbon NMR are recorded on a Brulcer AC 300 MHz using $CD_2Cl_2$ (from SDS) as solvent and $SiMe_4$ (from Aldrich) as internal standard. Melting point of solid salts is measured on a digital apparatus from Electrothermal.

c—Syntheses

The following salts are prepared according to known procedures (see e.g. for [EMI][Br], [EMI][Tf$_2$N], [EMI][CF$_3$SO$_3$], [BMI][Tf$_2$N]: Bonhôte, P.; Dias, A.-P.; Papageorgiou, N.; Kalyanasundaram, K.; Gratzel, M. *Inorg. Chem.*, (1996), 35, 1168-1178; for [BMI][BF$_4$]: Holbrey, J. D.; Seddon, K. R., *J. Chem. Soc., Dalton Trans.*, (1999), 2133-2139; for [BMI][PF$_6$]: Suarez, P. A. Z.; Dullius, J. E. L.; Einloft, S.; de Souza, R. F.; Dupont, J., *Polyhedron*, (1996), 15, 1217-1219).

EMI$^+$Br$^-$ (1-ethyl-3-methylimidazolium bromide),

EMI$^+$Tf$_2$N$^-$ (1-ethyl-3-methylimidazolium bistrifluoromethylsulphonylamide), EMI$^+$CF$_3$SO$_3^-$ (1-ethyl-3-methylimidazolium trifluoromethylsulphonate), BMI$^+$Cl$^-$ (1-n-butyl-3-methylimidazolium chloride), BMI$^+$PF$_6^-$ (1-n-butyl-3-methylimidazolium hexafluorophosphate), BMI$^+$Tf$_2$N$^-$ (1-n-butyl-3-methylimidazolium bistrifluoromethylsulphonylamide), and BMI$^+$BF$_4^-$ (1-n-butyl-3-methylimidazolium tetrafluoroborate).

Preparation Example 1

1-butyl-2,3-dimethylimidazolium Chloride [BMMI][Cl]

Freshly distilled 1-chlorobutane (88 g, 0.96 mol) is added in one portion to a 500 ml thick walled glass reactor equipped with a magnetic stirrer containing 1,2-dimethylimidazole (65 g, 0.68 mol). The reactor is sealed and the solution is stirred for 16 h at 100° C. (note: the reaction pressure is in excess of 2 atm.). Reactor is degassed and the hot solution is transferred (under argon) in a round bottom flask containing acetonitrile (95 ml). The solution is added drop wise under vigorous stirring to toluene (500 ml). A precipitate forms and is filtered out, washed with toluene (3×100 ml) and dried overnight under vacuum. [BMMI][Cl] is obtained (89.73 g, 70% yield) as a white hygroscopic solid.

$^1$H NMR (CD$_2$Cl$_2$): δ 0.97 [t, $^3$J=7.15 Hz, NCH$_2$CH$_2$CH$_2$CH$_3$]; 1.39 [sext, $^3$J=7.5 Hz, NCH$_2$CH$_2$CH$_2$CH$_3$]; 1.80 [quint, $^3$J=7.4 Hz, NCH$_2$CH$_2$CH$_2$CH$_3$]; 2.75 [s,CCH$_3$]; 4.00 [s, NCH$_3$]; 4.19 [t, $^3$J=7.1 Hz, NCH$_2$CH$_2$CH$_2$CH$_3$]; 7.52 [s, C H]; 7.84 [s, CH]; $^{13}$C NMR (CD$_2$Cl$_2$): δ 10.70 [NCH$_2$CH$_2$CH$_2$CH$_3$]; 13.74 [NCH$_2$CH$_2$CH$_2$CH$_3$]; 19.96 [NCH$_2$CH$_2$CH$_2$CH$_3$]; 32.26 [CCH$_3$]; 36.09 [NCH$_3$]; 48.94 [NCH$_2$CH$_2$CH$_2$CH$_3$]; 121.72 ; [CH]; 123.64 [CH]; 144.03 [CCH$_3$];

Elemental analysis (calculated): % C=57.14 (57.29), % H=9.08 (9.08), % N=14.85 (14.85).

Mp=104-105° C.

Preparation Example 2

1-butyl-2,3-dimethylimidazolium bistrifluoromethylsul phonylamide [BMMI][Tf$_2$N]:

A solution of lithium bis((trifluoromethyl)sulphonyl) amide (41.9 g, 0.149 mol) in 100 ml of H$_2$O is added drop wise to a solution of [BMMI][Cl] (24.32 g, 0.129 mol) in 150 ml of H$_2$O. The solution is stirred at 70° C. for 2 h and then cooled to room temperature. Methylene dichloride (50 ml) is added, and all is transferred to a separatory funnel. The lower phase (ionic liquid+CH$_2$Cl$_2$) is collected. Ionic liquid is purified through a short alumina column, and the CH$_2$Cl$_2$ removed on a Rotavapor. The resultant hydrophobic liquid is washed 3 times with 150 ml of H$_2$O and dried for 3 h at 50° C. under vacuum to afford [BMMI][Tf$_2$N] (44.1 g, 78.9% yield) as a colourless liquid.

$^1$H NMR (CD$_2$Cl$_2$): δ 0.97 [t, $^3$J=7.15 Hz, NCH$_2$CH$_2$CH$_2$CH$_3$]; 1.37 [sext, $^3$J=7.5 Hz, NCH$_2$CH$_2$CH$_2$CH$_3$]; 1.78 [quint, $^3$J=7.4 Hz, NCH$_2$CH$_2$CH$_2$CH$_3$]; 2.59 [s, CCH$_3$]; 3.79 [s, NCH$_3$]; 4.04 [t, $^3$J=7.1 Hz, NCH$_2$CH$_2$CH$_2$CH$_3$]; 7.19 [s, CH]; 7.21 [s, CH]; $^{13}$C NMR (CD$_2$Cl$_2$): δ 9.78 [NCH$_2$CH$_2$CH$_2$CH$_3$]; 13.53 [NCH$_2$CH$_2$CH$_2$CH$_3$]; 19.86 [NCH$_2$CH$_2$CH$_2$CH$_3$]; 31.90 [CCH$_3$]; 35.60 [NCH$_3$]; 49.00 [NCH$_2$CH$_2$CH$_2$CH$_3$]; 121.37 [CH]; 122.91 [CH]; 144.21 [CCH$_3$]; 120.50 [q, J$_{C-F}$=321.4 Hz, (CF$_3$SO$_2$)$_2$N];

Elemental analysis (calculated): % C=30.68 (30.49), % H=3.96 (3;95), % N=9.66 (9.70), % Cl<250 ppm (0)

Preparation Example 3

1-butyl-2,3-dimethylimidazolium tetrafluoroborate [BMMI][BF$_4$]

Procedure previously described for the synthesis of [BMMI][Tf$_2$N] is used (except the washes with water). From 22.23 g (0.118 mol) of [BMMI][Cl] and 15.52 g (0.141 mol) of sodium tetrafluoroborate, there are obtained 25.33 g (90% yield) of [BMMI][BF$_4$] as a colourless, very viscous and hydrophilic liquid.

$^1$H NMR (CD$_2$Cl$_2$): δ 0.96 [t, $^3$J=7.15 Hz, NCH$_2$CH$_2$CH$_2$CH$_3$]; 1.38 [sext, $^3$J=7.5 Hz, NCH$_2$CH$_2$CH$_2$CH$_3$]; 1.78 [quintet, $^3$J=7.4 Hz, NCH$_2$CH$_2$CH$_2$CH$_3$]; 2.60 [s, CCH$_3$]; 3.80 [s, NCH$_3$]; 4.06 [t, $^3$J=7.1 Hz, NCH$_2$CH$_2$CH$_2$CH$_3$]; 7.25 [dd, CH]; 7.30 [dd, CH]; $^{13}$C NMR (CD$_2$Cl$_2$): δ 9.58 [NCH$_2$CH$_2$CH$_2$CH$_3$]; 13.61 [NCH$_2$CH$_2$CH$_2$CH$_3$]; 19.79 [NCH$_2$CH$_2$CH$_2$CH$_3$]; 31.94 [CCH$_3$]; 35.36 [NCH$_3$]; 48.70 [NCH$_2$CH$_2$CH$_2$CH$_3$]; 121.30 [CH]; 122.88 [CH]; 144.31 [CCH$_3$].

Elemental analysis (calculated): % C=45.09 (45.03), % H=7.25 (7.14), % N=11.52 (11.67), % Cl=0.11 (0)

B—Catalysis a—Materials

Pd(OAc)$_2$ (98%) is purchased from Strem Chemicals, stored under argon and used without further purification. Triphenylphosphine (PPh$_3$) is obtained from Aldrich, trisodium tris((meta-sulphonatophenyl)phosphine) (TPPTS) from the lab reserves, bis(p-sulphonatophenyl)phenylphosphine dihydrate dipotassium salt (TPPDS) from Strem Chemical and diphenylphosphinobenzene-3-sulphonic acid sodium salt (TPPMS) from TCI. Those phosphines are stored under argon and used as such. Triethylamine (Fluka>98% ) and dimethyldodecylamine (Aldrich 97%) are distilled under argon, freeze-pumped and degassed with argon just before use. Water used in all experiments is deionised and degassed by freeze-pumping and bubbling of argon. Methanol is obtained by refluxing over Mg/I$_2$ and stored over 3 Å molecular sieves. Anhydrous ethylene glycol is obtained from Aldrich. Heptane was distilled over Na/K and stored over 3 Å molecular sieves under argon. Carbon dioxide (N45) and butadiene (N25) were obtained from "Air-Liquide" and used directly from cylinders.

b—Catalytic Experiments and Analyses: Catalytic Runs:

All catalytic reactions are performed in a 100 ml magnetically stirred stainless steel autoclave equipped with an inner glass sleeve and an internal thermocouple under argon atmosphere as shown in FIG. 1. In a typical reaction, Pd(OAc)$_2$, phosphine, ionic liquid, telogen (methanol ethylene glycol or water) and eventually heptane and/or amine are introduced in a Schlenk and then transferred into the purged autoclave via a ball valve. The autoclave is cooled to T<<−10° C. and the desired mass of butadiene is transferred from a lecture bottle resting on a scale (for telomerisation of butadiene with water reactions, this step is followed by the warming to room temperature of the autoclave in order to introduce 5 bar of carbon dioxide). The reactor is then heated to the desired reaction temperature. After the selected reaction time, the autoclave is cooled to 40° C. and butadiene is condensed in a volumetric glass cylinder cooled to −78° C. The volume of the liquid condensed in the cylinder (determined to be almost pure butadiene) is noted. The autoclave is then warmed to room temperature. The remaining liquid phases in the autoclave are recovered, weighed and further analyzed (GC, GC-MS and NMR).

Thus are obtained two measures of butadiene conversion, from the volume of unreacted butadiene condensed in the graduated cylinder (Conv. A) and the mass increase of the liquid solution in the autoclave (Conv. B). Conversion A is very often higher than conversion B due to possible loss of butadiene during trapping. Exact conversion will be considered as the average between conversion A and conversion B.

Work-up:

When at the end of the run only a single liquid phase is present, a sample is analysed without further treatment. When multiple phases are present, only the upper phase is analysed for product.

Analyses:

The identification of the telomerisation products is carried out both by Hewlett-Packard GC/MS and NMR analyses. Finally they are quantitatively analysed by gas chromatography on a HP6890 chromatograph equipped with FID detector and a HP1 column (L=30 m, internal diameter=0.32 mm, film thickness=0.25 µm). Injector temperature is 170° C. and detector temperature is 180° C. The temperature program is from 60° C. (3 min.) to 100° C. (0 min.) at a heating rate of 10° C./min. to 220° C. (30 min.) at a heating rate of 5° C./min.

c—Data Presentation

Abbreviations:
- OT: 1,3,7-octatriene and 1,3,6-octatriene
- VCH: 4-vinyl-cyclohexene
- Oligo.: products containing three and more units of butadiene
- 1-OMe: (cis+trans)-1-methoxy-2,7-octadiene
- 3-OMe: 3-methoxy-1,7-octadiene
- 1-Ol: 1-hydroxy-2,7-octadiene
- 3-Ol: 3-hydroxy-1,7-octadiene
- 1-OGly: (cis+trans) 1-hydroxy-2-(2,7-octadienyl-1-oxy) ethane
- 3-OGly: 1-hydroxy-2-(1,7-octadienyl-3-oxy) ethane
- (1+3)-Gly: bis(octadienyl-1-oxy)-1,2-ethane+bis(octadienyl-3-oxy)-1,2-ethane Conversions and Selectivities are Defined by the Following Equations:

Conv. A %: calculated from unreacted butadiene remaining after reaction $$\text{Conv. } A = \frac{\text{mass of butadiene introduced} - \text{mass of butadiene recovered}}{\text{mass of butadiene introduced}}$$

Conv. B %: calculated from the increase in the mass of the reactor $$\text{Conv. } B = \frac{\text{increase of the mass of reactor contents}}{\text{mass of butadiene introduced}}$$

GC selectivities toward products X are evaluated as:

$$GC. \text{ Sel. } (X) = \frac{\text{moles of product } X}{\sum (\text{moles of products})}$$

Selectivities to linear telomers (in the tables comprehensively reported as Ratio 1/3) are evaluated as:

$$\text{Ratio } 1/3 = \frac{\text{moles of linear telomer}}{\text{moles of branched telomer}}$$

Turn over number in mol $C_4H_6$/mol Pd is evaluated as:

$$TON = \frac{\text{mole of butadiene converted (average of Conv. } A \text{ and Conv. } B)}{\text{moles of palladium}}$$

Determination of the palladium leaching in the organic phase:

$$\% \text{ Pd leaching} = \frac{\text{mass of Pd in the organic phase}}{\text{mass of initial Pd}}$$

The analytical procedure consists in evaporating the organic products and solubilising the residue in a mixture of $HNO_3$/HCl. Palladium contained in this mixture is then quantified by ICP/SM.

d—Catalysis Examples (Cat Ex.) and Comparative Catalysis Examples (Comp. Cat. Ex.)

Using the telomerisation apparatus described above catalysis examples and comparative catalysis are carried out under the conditions indicated in the following.

Catalysis Examples 1 to 3

Catalysis examples 1 to 3 for telomerising 1,3-butadiene with methanol are run using $Pd(OAc)_2/PPh_3$ as the catalyst system. Table 1 shows the results.

TABLE 1

Telomerisation of 1,3-butadiene with methanol in the presence of $Pd(OAc)_2/PPh_3$[a]

| Cat Ex. | Ionic Liquid | Conv A | Conv B | time (h) | GC Sel. (mol %) | | | | Ratio 1/3 | TON |
|---|---|---|---|---|---|---|---|---|---|---|
| | | | | | 1-OMe + 3-OMe | VCH | OT | Olig. | | |
| 1 | [BMMI][BF$_4$] | 100 | 92 | 1 | 81.8 | 0.2 | 15.1 | 2.9 | 8 | 2619 |
| 2 | [BMMI][Tf$_2$N] | 100 | 89 | 1 | 84.0 | 0.2 | 13.7 | 2.1 | 9 | 2537 |

[a]Reaction conditions:
Pd(OAc)$_2$ = 30 mg (0.134 mmol);
PPh$_3$ = 105 mg (0.400 mmol);
Ionic liquid (4 ml);
MeOH = 15 ml (370 mmol);
C$_4$H$_6$ = 20 g (370 mmol);
T = 85° C.;

Excellent results are found for the 1,2,3-trialkylimidazolium ionic liquids regarding conversions and reaction rates (Cat. Ex. 1 and 2). Quantitative conversions are achieved after 1 h for the two solvents studied [BMMI][Tf$_2$N] and [BMMI][BF$_4$]. Selectivity toward telomers is around 83% and, again, there is a notable effect on the regioselectivity of the telomerisation reaction, the ratio 1-OMe/3-OMe in excess of 8-9. It seems that the nature of the anion of the salts (between the hydrophobic Tf$_2$N$^-$ salt and the hydrophilic BF$_4^-$ salt) does not induce any notable difference in terms of activity and selectivity. Furthermore, at the end of these reactions, absolutely no palladium black is observed. A two-phase liquid-liquid system remains in the case of 1,2,3-trialkylimidazolium salts. The lower phase corresponds to the ionic liquid whereas the upper one is a mixture of products and unreacted methanol.

Catalysis Examples 3 to 5

Catalysis examples 3 to 5 are run using Pd(OAc)$_2$ and water-soluble TPPMS as catalyst system. The results are shown in table 2.

TABLE 2

Telomerisation of 1,3-butadiene with methanol in the presence of Pd(OAc)$_2$/TPPMS[a]

| Cat. Ex. | Pd(OAc)$_2$ (mmol) | Temp. (°C.) | time (h) | Cnv A | Conv B | GC Sel. (mol %) | | | | Ratio 1/3 | TON |
|---|---|---|---|---|---|---|---|---|---|---|---|
| | | | | | | 1-OMe + 3-OMe | VCH | OT | Oligomers | | |
| 3 | 0.134 | 85 | 1 | 100 | 93 | 77.9 | 0.3 | 17.1 | 4.7 | 13.7 | 2769 |
| 4 | 0.028 | 85 | 5.75 | 85 | 80 | 77.7 | 0.8 | 20.9 | 0.6 | 16.0 | 11092 |
| 5 | 0.025 | 110 | 5.75 | 89 | 75 | 50.4 | 3.0 | 41.8 | 4.8 | 11.7 | 11953 |

[a]Reaction conditions:
TPPMS = 3 eq/Pd;
[BMMI][Tf$_2$N] (4 ml);
MeOH = 15 ml (370 mmol);
C$_4$H$_6$ = 20 g (370 mmol);

The use of TPPMs leads to single phase system at 93% conversion (Cat. Ex. 3). Selectivity toward telomer is lower with TPPMS than with TPP, 77.9 against 84.0%. However with TPPMS the ratio 1-OMe/3-OMe is largely better, 13.7. The addition of 16% wt (10 ml) of heptane to the solution obtained in Cat. Ex. 3 leads to clean separation of an ionic liquid phase from the product/MeOH/heptane phase.

Catalysis Examples 6 to 8

Catalysis examples 6 to 8 are run in the presence of n-heptane using Pd(OAc)$_2$ and different phosphines. The palladium leaching into the organic phase is determined by microanalysis of the two phases. The results are shown in table 3.

TABLE 3

Telomerisation of 1,3-butadiene with methanol in the presence of n-heptane using Pd(OAc)$_2$/and different phosphines[a]

| Cat. Ex. | P | Conv A | Conv B | GC Sel. (mol %) | | | | Ratio 1/3 | % Pd leaching | TON |
|---|---|---|---|---|---|---|---|---|---|---|
| | | | | 1-OMe + 3-OMe | VCH | OT | Oligo. | | | |
| 6 | TPP | 82 | 71 | 53.3 | — | 40.6 | 6.1 | 14.6 | 14.2 | 2127 |
| 7 | TPPMS | 74 | 66 | 70.3 | 0.6 | 14.1 | 15.0 | 13.1 | 1.9 | 1816 |
| 8 | TPPDS | 56 | 51 | 58.6 | 1.2 | 17.5 | 22.8 | 15.0 | 1.8 | 1373 |

[a]Reaction conditions:
Pd(OAc)$_2$ = 30 mg (0.134 mmol);
Phosphine = 3 eq/Pd;
[BMMI][Tf$_2$N] (4 ml);
MeOH = 7.5 ml (185 mmol);
heptane = 10 ml;
C$_4$H$_6$ = 20 g (370 mmol);
t = 3 h;
T = 85° C.;

Catalysis Examples 9 to 13

The product phase of catalysis example 7 is decanted and the palladium contained in the ionic liquid phase is reintroduced to the reactor with fresh reactants and co-solvent. Microanalysis of the organic phase at the end of each catalysis example 10 to 14 indicates 1-4% leaching of palladium to the organic phase. Slight changes in activity are observed with each cycle. At first, activities are actually higher (catalysis examples 10 to 12) perhaps as the initiation reactions (conversion of Pd(OAc)2 to the active species) reach completion. Activity slowly degrades in catalysis examples 12 and 13, in part perhaps due to the mechanical difficulty of quantitatively recuperating the ionic liquid phase (drops of the liquid can remain in the Schlenk tube used for decantation and/or syringe), palladium leaching, or to some palladium deactivation. In no case is there obvious evidence for the formation of palladium black. The results are shown in table 4.

TABLE 4

Telomerisation of 1,3-butadiene with methanol in the presence of n-heptane using recycled ionic liquid phase[a]

| Cat. Ex. | Conv A | Conv B | GC Sel. (mol %) | | | | Ratio 1/3 | TON |
|---|---|---|---|---|---|---|---|---|
| | | | 1-OMe + 3-OMe | VCH | OT | Oligo. | | |
| 9 | 74 | 66 | 70.3 | 0.6 | 14.1 | 15.0 | 13.1 | 1816 |
| 10 | 82 | 73 | 72.2 | 0.5 | 13.2 | 14.2 | 12.4 | 2001 |

TABLE 4-continued

Telomerisation of 1,3-butadiene with methanol in the presence of
n-heptane using recycled ionic liquid phase[a]

| Cat. Ex. | Conv A | Conv B | 1-OMe + 3-OMe | VCH | OT | Oligo. | Ratio 1/3 | TON |
|---|---|---|---|---|---|---|---|---|
| 11 | 89 | 81 | 72.4 | 0.4 | 15.9 | 11.3 | 15.4 | 2249 |
| 12 | 80 | 68 | 75.6 | 0.5 | 16.2 | 7.7 | 16.3 | 1907 |
| 13 | 70 | 63 | 78.8 | 0.9 | 17.3 | 3.1 | 18.6 | 1709 |

[a]Reaction conditions:
$Pd(OAc)_2$ = 30 mg (0.134 mmol);
TPPMS = 146 mg (0.401 mmol);
[BMMI][$Tf_2N$] (4 ml);
MeOH = 7.5 ml (185 mmol);
heptane = 10 ml;
$C_4H_6$ = 20 g (370 mmol);
T = 85° C.;
t = 3 h.

Comparative Catalysis Examples 1 to 5

Comparative catalysis examples 1 to 5 are run using 1,3-dialkylimidazolium salts. The results are shown in table 5.

TABLE 5

Telomerisation of 1,3-butadiene with methanol using $Pd(OAc)_2/PPh_3$ as a
catalyst system in the presence of 1,3-dialkylimidazolium salts as ionic liquid[a]

| Comp. Cat Ex. | Ionic Liquid | Conv A | Conv B | 1-OMe + 3-OMe | VCH | OT | Oligo. | Ratio 1/3 | TON |
|---|---|---|---|---|---|---|---|---|---|
| 1 | [BMI][$Tf_2N$][b] | 10 | 7 | 62.0 | 18.4 | 3.5 | 16.1 | 7.8 | 241 |
| 2 | [EMI][$Tf_2N$][b] | 7 | 3 | 66.1 | 21.6 | 1.7 | 10.6 | 5.8 | 146 |
| 3 | [EMI][$Tf_2N$][c] | 16 | 6 | 27.5 | 44.7 | 0.6 | 27.1 | 6.5 | 271 |
| 4 | [BMI][$BF_4$][c] | 15 | −1 | 49.6 | 33.9 | 1.2 | 15.4 | 5.1 | 165 |
| 5 | [EMI][$PF_6$][d] | 13 | 2 | 38.0 | 49.8 | 8.2 | 4.0 | 7 | 184 |

[a]Reaction conditions:
$Pd(OAc)_2$ = 30 mg (0.134 mmol);
$PPh_3$ = 105 mg (0.400 mmol);
MeOH = 15 ml (370 mmol);
$C_4H_6$ = 20 g (370 mmol);
T = 85°C.;
t = 22 h.
[b]1 ml of ionic liquid;
[c]4 ml of ionic liquid;
[d]Ionic liquids purchased from Aldrich (97% pure, white solid, equivalent of 1 ml of ionic liquid)

Conversions are extremely low. There is, however, no obvious formation of palladium black: systems, at the end of the reaction, appear as homogeneous quite colourless liquids. The "palladium-phosphine" catalyst supposed to be formed in situ certainly suffered of some modifications and so deactivation. The possible contamination of halide impurities from the ionic liquid is first evoked. Indeed, synthesis of some ionic liquids is based on the use of chloride intermediates, potentially present in the remaining salts. However, this hypothesis can be totally excluded to explain this phenomenon. Indeed the halide contents of ionic liquids are always under the detection limit (50-250 ppm) which would be too little for total contamination of the catalyst. Moreover, this behaviour is observed with both commercial salts (Comp. Cat. Ex. 5) and ionic liquids synthesised in the laboratory which exclude any questions concerning purity of salts used in those experiments.

Comparative Catalysis Examples 6 to 9

Comparative catalysis examples 6 to 9 are run using 1,3-dialkylimidazolium salts and different phosphine/palladium ratios in order to determine their influence on the conversion and selectivity. The results are shown in table 6.

TABLE 6

Telomerisation of 1,3-butadiene with methanol using $Pd(OAc)_2/PPh_3$ with
different Pd/phosphine ratios as a catalyst system in the presence of 1,3-
dialkylimidazolium salts as ionic liquid[a]

| Comp. Cat. Ex. | P/Pd ratio | Conv A | Conv B | 1-OMe + 3-OMe | VCH | OT | Oligo. | Ratio 1/3 | TON |
|---|---|---|---|---|---|---|---|---|---|
| 6 | 3 | 11 | 1 | 56.2 | 32.9 | 1.7 | 9.2 | 5.9 | 166 |
| 7 | 4 | 11 | 5 | 72.9 | 27.1 | — | — | 5.9 | 228 |
| 8 | 10 | 26 | 19 | 73.0 | 9.9 | — | 17.1 | 6.5 | 593 |
| 9 | 20 | 30 | 23 | 71.0 | 12.7 | 2.3 | 14.0 | 6.5 | 745 |

[a]Reaction conditions:
$Pd(OAc)_2$ = 30 mg (0.134 mmol);
[EMI][$Tf_2N$] (1 ml);
MeOH = 15 ml (370 mmol);
$C_4H_6$ = 20 g (370 mmol);
T = 85° C.;
t = 22 h.

Again, even with a large excess of PPh$_3$ performances of the catalytic system remain very low. With 20 equivalents of phosphine per palladium, conversion does not exceed 26% (Comp. Cat. Ex. 9).

Catalysis Examples 14 and 15

Catalysis examples 14 to 15 for telomerising 1,3-butadiene with glycol in the presence of n-heptane are run using Pd(OAc)$_2$/TPPMS as the catalyst system. Table 7 shows the results.

TABLE 7

Telomerisation of 1,3-butadiene with Glycol in the presence of n-heptane using Pd(OAc)$_2$/TPPMS as a catalyst system[a]

| Cat. Exp. | Conv A | Conv B | 1-OGly + 3-OGly | GC Sel. (mol %) VCH | OT | Oligo. | (1 + 3)-OGly[2] | Ratio 1/3 | TON |
|---|---|---|---|---|---|---|---|---|---|
| 14[b] | 96 | 87 | 67.6 | 5.2 | 4.2 | 1.7 | 21.3 | 24 | 2767 |
| 15[c] | 93 | 81 | 79.9 | — | 6.9 | — | 13.2 | 26 | 2482 |

[a]Reaction conditions:
Pd(OAc)$_2$ = 30 mg (0.134 mmol);
TPPMS = 0.146 g (0.401 mmol);
Glycol = 10.5 ml (185 mmol);
[BMMI][Tf$_2$N] = 4 ml;
C$_4$H$_6$ = 20 g (370 mmol);
T = 85° C.;
t = 45 min.;
[b]heptane 10 ml
[c]heptane 30 ml.

Catalysis Examples 16 and 17

Catalysis example 16 for telomerising 1,3-butadiene with water are run using Pd(OAc)$_2$/TPPMS as the catalyst system. Table 8 shows the results.

TABLE 8

Telomerisation of 1,3-butadiene with water using Pd(OAc)$_2$/TPPMS as a catalyst system[a]

| Ref. ML | Amine | Heptane (ml) | Conv A | Conv B | Octadienols | % GC. (mol) VCH | OT | Oligo. | Ratio (1/3) | TON |
|---|---|---|---|---|---|---|---|---|---|---|
| 121[b] | NEt$_3$[d] | — | 95 | 95 | 74.0 | — | 18.8 | 7.2 | 17 | 1164 |
| 133[c] | NEt$_3$[d] | 30 | 78 | 70 | 67.9 | <0.1 | 32.1 | <0.1 | 18 | 961 |

[a]Reaction conditions:
Pd(OAc)$_2$ = 0.050 g (0.223 mmol);
TPPMS = 324 mg (0.892 mmol);
[BMMI][BF$_4$] = 4 ml;
C$_4$H$_6$ = 15 g (278 mmol);
H$_2$O = 5 g (278 mmol);
P$_{CO2}$ = 5 bar;
T = 85° C.;
[b]t = 3 h;
[c]t = 5 h;
[d]NEt$_3$ = 50 eq/Pd;

Catalysis Examples 18 and 21

Catalysis example 21 for dimerisation—oligomerisation of 1,3-butadiene are run using Pd(OAc)$_2$ as the catalyst system. Table 9 shows the results.

TABLE 9

Oligomerisation of 1,3-butadiene using Pd(OAc)$_2$ as a catalyst system[a]

| Cat. Ex. | Ionic Liquid | Conv A | Conv B | % GC. (mol) VCH | OT | Butadiene trimers | Olig. | TON |
|---|---|---|---|---|---|---|---|---|
| 18 | [EMI][Tf$_2$N] | 41 | 34 | 29.9 | 10.6 | 39.2 | 20.3 | 463 |
| 19 | [BMI][BF$_4$] | 9 | 8 | 52.4 | 9.6 | 8.6 | 29.4 | 106 |
| 20 | [BMI][PF$_6$] | 38 | 33 | 34.7 | 8.7 | 28.3 | 28.3 | 520 |
| 21 | [BMMI][Tf$_2$N] | 70 | 67 | 70.9 | 6.3 | 10.7 | 12.1 | 727 |

[a]Reaction conditions:
Pd(OAc)$_2$ = 0.050 g (0.223 mmol);
Ionic liquids = 4 ml;
C$_4$H$_6$ = 15 g (278 mmol);
H$_2$O = 5 g (278 mmol);
P$_{CO2}$ = 5 bar;
T = 85° C.;
t = 22 h;

In terms of butadiene conversion, one will note that the use of BMMI+Tf2N- considerably increases the conversion.

The invention will now be described in greater detail with the aid of embodiments given as non-limiting examples.

The invention claimed is:

1. A method of conducting a catalysed organic chemical reaction, comprising: providing a reactant with a solvent, wherein the solvent is selected from the group consisting of 1,2,3-substituted imidazolium salts, 1,2,3,4-substituted imidazolium salts, and 1,2,3,4,5-substituted imidazolium salts, and
with the exception that said solvent is not
1,2,3,4,5-pentamethylimidazolium salts with sulphonated or carboxylated triesters or phosphorous,
1,2,3,4,5-tetramethyl-4H-imidazolium salts with sulphonated or carboxylated triesters or phosphorous,
1,2,3,4-tetramethyl-5H-imidazolium salts with sulphonated or carboxylated triesters or phosphorous, and
1-trimethylsilyl-2,3,5-trimethyl-4H-imidazolium salts with sulphonated or carboxylated triesters or phosphorous, and
obtaining a product from said catalysed organic chemical reaction,
wherein the catalysed organic chemical reaction is selected from the group consisting of a method for catalytic conversion of olefins, a condensation reaction, a hydrogenation reaction, an isomerisation reaction, a Suzuki cross-coupling reactions, an amination reaction, a partial oxidation of alkanes, a kinetic resolution of racemic mixtures, a hydrogenation of imines, a hydrogenation of ketones, a transfer hydrogenation, or hydroxylation of aromatic organic compounds.

2. The method according to claim 1 wherein the 1,2,3-substituted imidazolium salts, 1,2,3,4-substituted imidazolium salts or 1,2,3,4,5-substituted imidazolium salts are of the following formula (1):

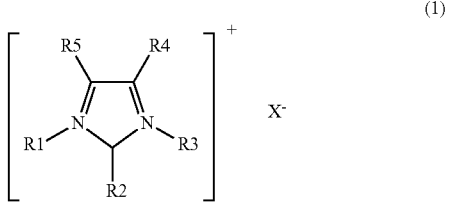

wherein $R^1$ and $R^3$ are the same or different and are each selected from the group consisting of a chiral or achiral alkyl group having up to 10 carbon atoms, a chiral or achiral cycloalkyl group of 4 to 10 carbon atoms, a chiral or achiral aryl group of 6 to 10 carbon atoms, and a chiral or achiral tri(C1-C10) alkylsilyl group,
$R^2$ is selected from the group consisting of a chiral or achiral alkyl group having up to 10 carbon atoms, a chiral or achiral cycloalkyl group of 4 to 10 carbon atoms, a chiral or achiral aryl group of 6 to 10 carbon atoms, a halogen atom, an alkyl group, a cycloalkyl group and an aryl group as defined above,
$R^4$ and $R^5$ are the same or different and are each selected from the group consisting of hydrogen, a chiral or achiral alkyl group having up to 10 carbon atoms, a chiral or achiral cycloalkyl group of 4 to 10 carbon atoms, a chiral or achiral aryl group of 6 to 10 carbon atoms, a chiral or achiral tri(C1-C10)alkylsilyl group, a halogen atom, hydrogen, an alkyl group, a cycloalkyl group, an aryl group, or a tri(C1-C10) alkylsilyl group;
and $X^-$ represents an anion.

3. The method according to claim 2 wherein:
$R^1$, $R^2$ and $R^3$, identical or different, are each independently chosen from (C1-C6)alkyl,(C1-C6)haloalkyl and cycloalkyl;
$R^4$ and $R^5$, identical or different, are each independently chosen from hydrogen, (C1-C6) alkyl, (C1-C6)haloalkyl and cycloalkyl;
and $X^-$ represents an anion.

4. The method according to claim 2 wherein:
$R^1$, $R^2$, and $R^3$, identical or different, are each independently chosen from methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;
$R^4$ and $R^5$, identical or different, are each independently chosen from hydrogen, methyl, ethyl, propyl, iso-propyl, butyl, sec-butyl, 1-pentyl, 2-pentyl, 3-pentyl, iso-pentyl, hexyl, iso-hexyl, cyclohexyl, trifluoromethyl, 1,1,1-trifluoroethyl, perfluoroethyl, perfluoropropyl, 1,1,1,2,2,3,3-heptafluorobutyl, and perfluorobutyl;
and X-represents an anion.

5. The method according to claim 2, wherein X is an anion selected from the group consisting of fluoride, chloride, bromide, iodide, hexafluorophosphate, hexafluoroatimonate, hexafluoroarsenate, fluorosulphonate, tetrafluoroborate, bisperfluoro (C1-C10) alkylsulphonyl amides, perfluoro(C1-

C10) alkyl sulphonates, dichlorocuprate, tetrachloroborate, tetrachloroaluminate, heptachlorodialuminate ($Al_2Cl_7$), trichlorozincate, and anions of sulphonated or carboxylated (alkyl and/or aryl)-phosphines or phosphites.

6. The method according to claim 2, wherein X is an anion selected from the group consisting of fluoride, chloride, bromide, iodide, hexafluorophosphate, fluorosulphonate, tetrachloroborate, tetrafluoroborate, bisperfluoro (C1-C10)alkylsulphonyl amides, perfluoro (C1-C10)alkyl sulphonates, and anions of sulphonated or carboxylated (alkyl, cycloalkyl and/or aryl)-phosphines or -phosphites.

7. The method according to claim 1, wherein the 1,2,3 substituted imidazolium salts are 1,2,3-tri (C1-C10) alkyl-imidazolium salts.

8. The method according to claim 1, wherein the 1,2,3 substituted imidazolium salts are selected from the group consisting of 1-ethyl-2,3-dimethylimidazolium bromide, 1-ethyl-2,3-dimethylimidazolium bistrifluoromethylsulphonylamide, 1-ethyl-2,3-dimethylimidazolium trifluoromethylsulphonate, 1-n-butyl-2,3-dimethylimidazolium chloride, 1-n-butyl-2,3-dimethylimidazolium hexafluorophosphate, 1-n-butyl-2,3-dimethylimidazolium bistrifluoromethylsulphonylamide, and 1-n-butyl-2,3-methylimidazolium tetrafluoroborate.

9. The method according to claim 1, wherein the 1,2,3 substituted imidazolium salts are a 1-n-butyl-2,3-dimethylimidazolium salt.

10. The method according to claim 1 wherein the 1,2,3 substituted imidazolium salts are selected from the group consisting of 1-n-butyl-2,3-dimethylimidazolium chloride, 1-n-butyl-2,3-dimethylimidazolium hexafluorophosphate, 1-n-butyl-2,3-dimethylimidazolium bistrifluoromethyl-sulphonylamide and 1-n-butyl-2,3-methylimidazolium tetrafluoroborate.

11. The method according to claim 1, wherein the catalysed organic reaction is a method for the reaction of catalytic conversion of olefins selected from the group consisting of telomerisation of conjugated dienes, dimerisation of olefins, oligomerisation of olefins, polymerization of olefins, alkylation of olefins, hydrogenation of olefins, olefin metathesis, hydroformylation of olefins, ring-closing metathesis of olefins, ring-opening metathesis polymerisation of olefins, symmetric or asymmetric epoxidation of olefins (including heteroatom substituted olefins), or cyclopropanation of olefins.

12. The method according to claim 1, wherein 1,2,3-substituted imidazolium salts, 1,2,3,4-substituted imidazolium salts or 1,2,3,4,5-substituted imidazolium salts, with the exception of 1,2,3,4,5-pentamethyl imidazolium-, 1,2,3,5-tetramethyl-4H-imidazolium-, 1,2,3,4-tetramethyl-5H-imidazolium, and 1-trimethylsilyl-2,3,5-trimethyl-4H imidazolium salts with sulphonated or carboxylated triesters of phosphorous acid are a catalyst or catalyst component.

13. The method according to claim 1, wherein the catalysed organic reaction is a two-phase catalytic reaction.

14. The method according to claim 1, wherein the catalysed organic reaction is catalysed with a metal-containing compound, and is selected from the group consisting of the catalytic conversion of olefins, telomerisation of conjugated dienes, dimerisation of olefins, oligomerisation of olefins, polymerization of olefins, alkylation of olefins, hydrogenation of olefins, olefin metathesis, hydroformylation of olefins, ring-closing metathesis of olefins, ring-opening metathesis polymerisation of olefins, the symmetric or asymmetric epoxidation of olefins (including heteroatom substituted olefins) and cyclopropanation of olefins, condensation reaction, hydrogenation reaction, isomerisation reaction, Suzuki cross-coupling reactions, amination reaction, partial oxidation of alkanes, kinetic resolution of racemic mixtures, hydrogenation of imines, hydrogenation of ketones, transfer hydrogenation and hydroxylation of aromatic organic compounds.

15. A composition comprising a metal compound, a phosphorous-containing compound and an imidazolium salt as solvent, said imidazolium salt of the following formula (1):

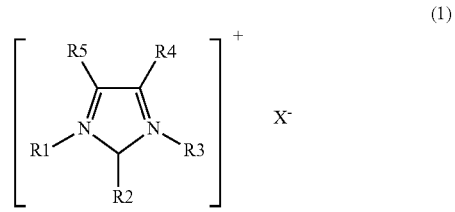

(1)

wherein $R^1$ and $R^3$ are the same or different and are each selected from the group consisting of a chiral or achiral alkyl group having up to 10, a chiral or achiral cycloalkyl group of 4 to 10 carbon atoms, a chiral or achiral aryl group of 6 to 10 carbon atoms, and a chiral or achiral tri (C1-C10) alkylsilyl group, $R^2$ is selected from the group consisting of a chiral or achiral alkyl group having up to 10, a chiral or achiral cycloalkyl group of 4 to 10 carbon atoms, a chiral or achiral aryl group of 6 to 10 carbon atoms, and a halogen atom, $R^4$ and $R^5$ are the same or different and are each selected from the group consisting of hydrogen, a chiral or achiral alkyl group having up to 10, a chiral or achiral cycloalkyl group of 4 to 10 carbon atoms, a chiral or achiral aryl group of 6 to 10 carbon atoms, a chiral or achiral tri (C1-C10) alkylsilyl group, and a halogen atom;

and wherein X is an anion selected from the group consisting of fluoride, chloride, bromide, iodide, hexafluorophosphate, hexafluoroantimonate, hexafluoroarsenate, fluorosulphonate, tetrafluoroborate, bisperfluoro (C1-C10)) alkylsulphonyl amides, perfluoro (C1-C10) alkyl sulphonates, dichlorocuprate, tetrachloroborate, tetrachloroaluminate, heptachlorodialuminate ($Al_2Cl_7$), trichlorozincate, and anions of sulphonated or carboxylated (alkyl and/or aryl)-phosphines or phosphites, and with the exception of 1,2,3,4,5-pentamethylimidazolium-, 1,2,3,5-tetramethyl- 4H-imidazolium-, 1,2,3,4-tetramethyl-5H-imidazolium, 1-trimethylsilyl-2,3,5-trimethyl-4H-imidazolium-salts of sulphonated or carboxylated triesters of phosphorous acid, 1,2,3,4,5-pentamethylimidazolium iodide, 1,2,3-trimethylimidazolium] bromide, 1,2,3-trimethylimidazolium iodide, 1,2-dimethyl-3-ethylimidazolium bromide, 1,2-dimethyl-3-ethylimidazolium chloride, 1,2-dimethyl-3-butylimidazolium fluoride, 1-butyl-2,3-dimethylimidazolium salt of 2,2'- (2,5-cyclohexadiene-1,4-ylidene) bis [propane-dinitrile], 1,3-dimethyl-2,4,5-trichloro-imidazolium tetrafluoroborate, 1,3-dimethyl-2,4,5-tribromo-imidazolium tetrafluorofluoroborate, or 1,3-dimethyl-2,4,5-tribromo-imidazolium bromide.

16. An imidazolium salt of the composition according to claim 15 selected from the group consisting of 1-ethyl-2,3-dimethylimidazolium bromide, 1-ethyl-2,3-dimethylimidazolium bistrifluoromethylsulphonylamide, 1-ethyl-2,3-dimethylimidazolium trifluoromethylsulphonate, 1-n-2,3-dimethylimidazolium chloride, 1-n-butyl-2,3-dimethylimidazolium hexafluorophosphate, 1-n-butyl-2,3- dimethylimidazolium bistrifluoromethylsulphonylamide, and 1-n-butyl-2,3-methylimidazolium tetrafluoroborate.

17. An imidazolium salt of the composition according to claim 15, selected from the group consisting of 1-n-butyl-2,3-dimethylimidazolium bistrifluoro (C1-C10) alkylsulphonylamide, 1-n-butyl-2,3-dimethylimidazolium tetrafluoroborate and 1-n-butyl-2,3-dimethyimidazolium hexafluorophosphate.

* * * * *